(12) United States Patent
Lu et al.

(10) Patent No.: US 11,761,077 B2
(45) Date of Patent: Sep. 19, 2023

(54) SPUTTERING TECHNIQUES FOR BIOSENSORS

(71) Applicant: MEDTRONIC MINIMED, INC., Northridge, CA (US)

(72) Inventors: Kelly Lu, Plymouth, MN (US); Lea Ann Nygren, Bloomington, MN (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 710 days.

(21) Appl. No.: 16/052,467

(22) Filed: Aug. 1, 2018

(65) Prior Publication Data
US 2020/0040443 A1 Feb. 6, 2020

(51) Int. Cl.
| C23C 14/14 | (2006.01) |
| C23C 14/02 | (2006.01) |
| C23C 14/08 | (2006.01) |
| C23C 14/20 | (2006.01) |
| C23C 14/34 | (2006.01) |
| C23C 14/56 | (2006.01) |
| A61B 5/00 | (2006.01) |
| A61B 5/145 | (2006.01) |
| A61B 5/1486 | (2006.01) |

(52) U.S. Cl.
CPC ............ *C23C 14/14* (2013.01); *C23C 14/025* (2013.01); *C23C 14/08* (2013.01); *C23C 14/083* (2013.01); *C23C 14/205* (2013.01); *C23C 14/34* (2013.01); *C23C 14/562* (2013.01); *A61B 5/0022* (2013.01); *A61B 5/14503* (2013.01); *A61B 5/14532* (2013.01); *A61B 5/14865* (2013.01); *A61B 2562/125* (2013.01)

(58) Field of Classification Search
CPC ....... C23C 14/14; C23C 14/083; C23C 14/08; C23C 14/025; C23C 14/562
See application file for complete search history.

(56) References Cited

U.S. PATENT DOCUMENTS

| 4,755,173 | A |   | 7/1988 | Konopka et al. |
| 5,118,400 | A | * | 6/1992 | Wollam ................ C23C 14/022 204/192.11 |
| 5,391,250 | A |   | 2/1995 | Cheney, II et al. |
| 5,485,408 | A |   | 1/1996 | Blomquist |
| 5,522,803 | A |   | 6/1996 | Teissen-Simony |
| 5,665,065 | A |   | 9/1997 | Colman et al. |
| 5,800,420 | A |   | 9/1998 | Gross et al. |
| 5,807,375 | A |   | 9/1998 | Gross et al. |
| 5,844,347 | A | * | 12/1998 | Takayama ................ H03H 3/08 310/313 R |
| 5,925,021 | A |   | 7/1999 | Castellano et al. |
| 5,954,643 | A |   | 9/1999 | Van Antwerp et al. |

(Continued)

OTHER PUBLICATIONS

Machine Translation JP 63300954 A (Year: 1988).*

(Continued)

*Primary Examiner* — Michael A Band
(74) *Attorney, Agent, or Firm* — GATES & COOPER LLP

(57) ABSTRACT

Systems and methods for forming probes for a biosensor. In the systems and methods disclosed herein, a base substrate is provided; and a platinum layer is formed on the base substrate by sputtering platinum in the absence of oxygen. The platinum layer is formed using a sputtering pressure of at least 30 mtorr.

10 Claims, 12 Drawing Sheets

(56) References Cited

U.S. PATENT DOCUMENTS

| | | | |
|---|---|---|---|
| 5,981,390 A * | 11/1999 | Lee | C23C 14/14 438/650 |
| 6,017,328 A | 1/2000 | Fischell et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 9,237,961 B2 * | 1/2016 | Mitchell | A61F 2/958 |
| 2007/0123819 A1 | 5/2007 | Mernoe et al. | |
| 2010/0160861 A1 | 6/2010 | Causey, III et al. | |
| 2018/0030499 A1 * | 2/2018 | Hori | C12Q 1/006 |

OTHER PUBLICATIONS

DERWENT Abstract: JP 63300954 A, Yoshii (Year: 1988).*

Slavcheva, E.; Ganske, G.; Topalov, G.; Mokwa, W.; Schnakenberg, U. "Effect of sputtering parameters on surface morphology and catalytic efficiency of thin platinum films". Applied Surface Science, vol. 255, p. 6479-6486. (Year: 2009).*

* cited by examiner

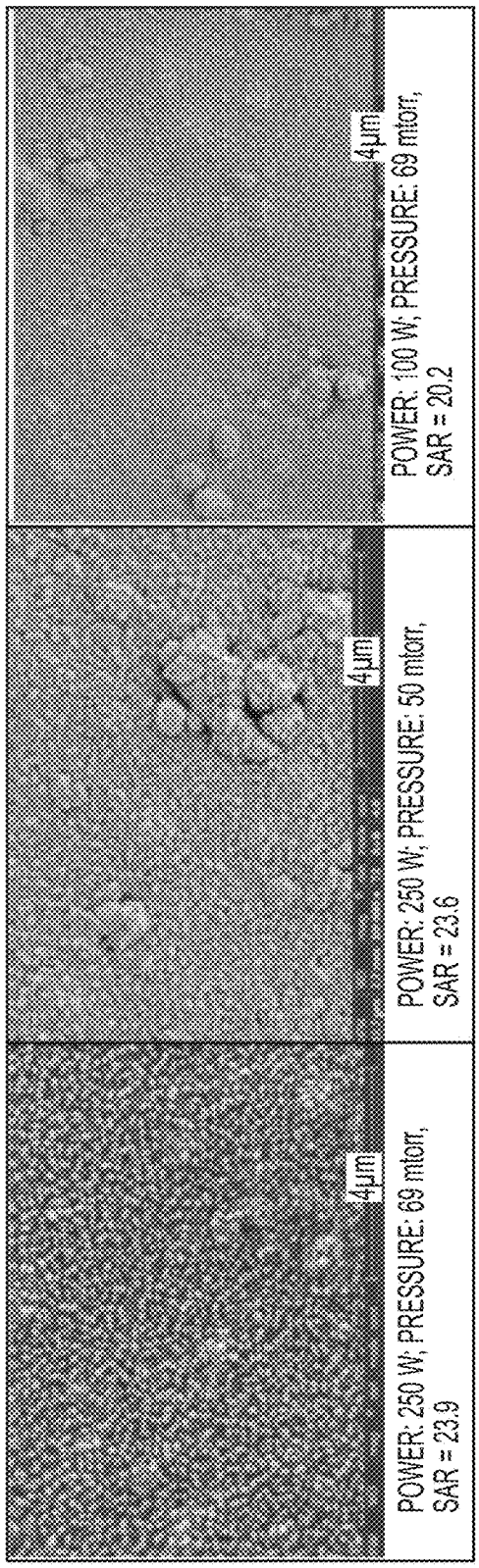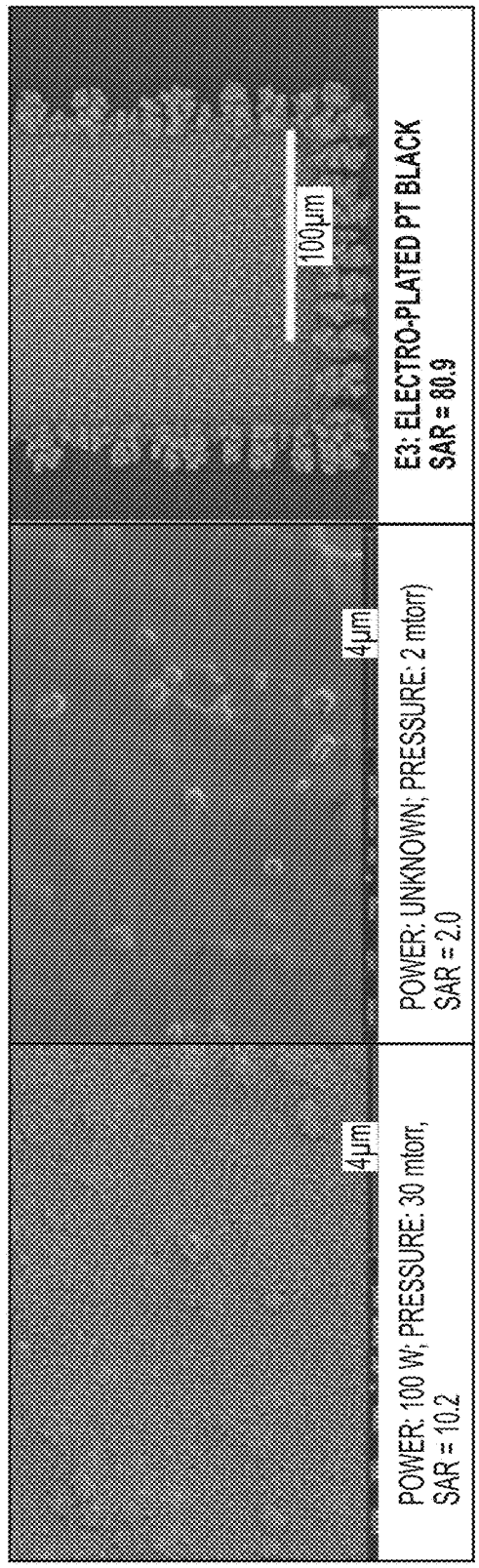

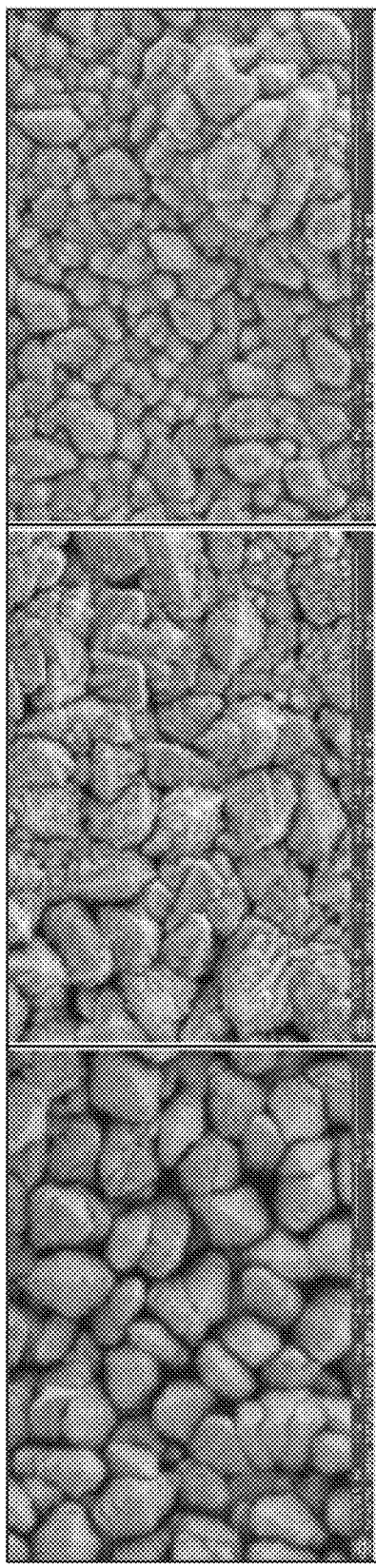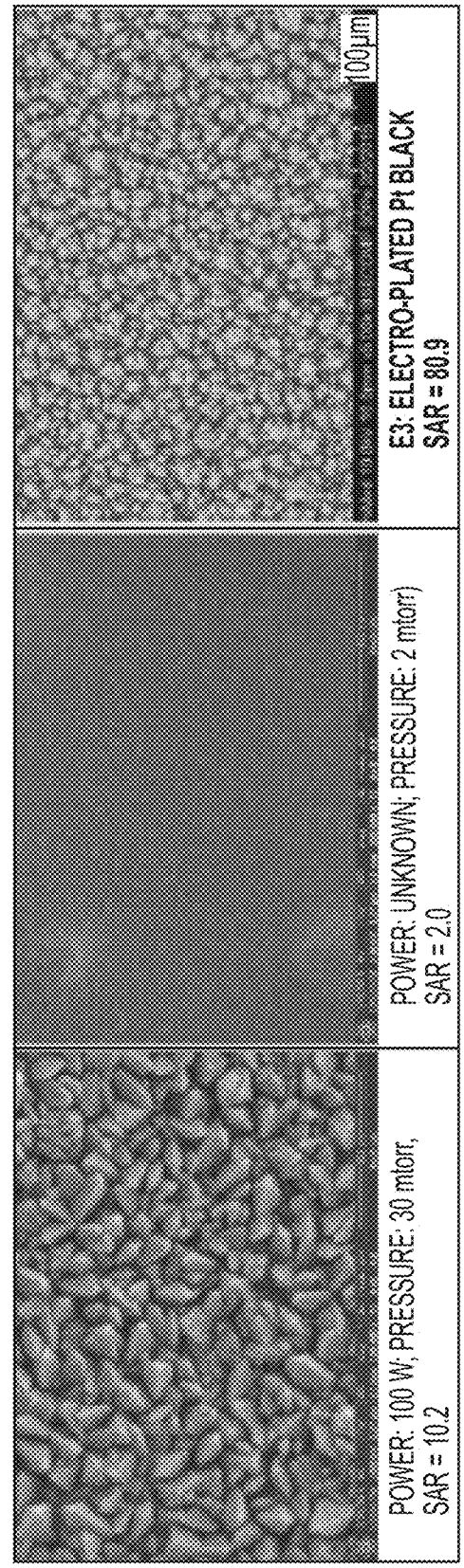

SPUTTERING TECHNIQUES FOR BIOSENSORS

TECHNICAL FIELD

Embodiments of the subject matter described herein relate generally to biosensors. More particularly, embodiments of the subject matter relate to biosensors having probes with one or more sputtered layers.

BACKGROUND

Needle-implantable biosensors have shown to be useful for continuous glucose monitoring applications in diabetes management.

So-called "first-generation" needle-implantable glucose biosensors operate by monitoring the amount of $H_2O_2$ which is produced from the catalyzed reaction of glucose by $GO_x$ to gluconic acid and $H_2O_2$ in the following reaction steps:

$$Glucose + GO_x(FAD) \rightarrow Glucorolactone + GO_x(FADH_2) \quad (1)$$

$$GO_x(FADH_2) + O_2 \rightarrow GO_x(FAD) + H_2O_2 \quad (2)$$

The product $H_2O_2$ is then electrochemically oxidized on the working electrode surface of a probe of the biosensor. The blood glucose concentration can be correlated to the signal obtained from the oxidation of the $H_2O_2$, or to the electrochemical reduction of $O_2$, via the reversible reaction:

$$H_2O_2 \leftrightharpoons 2H^+ + O_2 + 2e^-$$

In order to accurately detect the signal obtained from the oxidation of $H_2O_2$, it is desirable for the working electrode to have a high sensitivity to $H_2O_2$. A high sensitivity to $H_2O_2$ allows for a high signal-to-noise ratio of the signal produced through the detection of the amount of $H_2O_2$, and therefore a more accurate and reliable blood glucose concentration may be determined. Conventionally, the working electrode of the probe of the glucose biosensor is formed of platinum, which can be manufactured to have a high sensitivity to $H_2O_2$.

Platinum is typically incorporated into the probe of the glucose biosensor either by forming a probe from a platinum alloy or by electroplating platinum onto a base substrate of the probe.

Forming the probe from a platinum alloy or electroplating platinum onto a base substrate are both expensive, time-consuming manufacturing processes. In particular, the more commonly-used technique of electroplating is a discontinuous "batch" manufacturing process which requires the use of relatively expensive solutions, and which has a degree of batch-to-batch variability with regard to the sensitivity of the electroplated probe to $H_2O_2$.

Accordingly, it is desirable to manufacture probes for glucose biosensors that have a required level of sensitivity to $H_2O_2$ in a cheaper, faster and simpler manufacturing process.

Furthermore, other desirable features and characteristics will become apparent from the subsequent detailed description and the appended claims, taken in conjunction with the accompanying drawings and the foregoing technical field and background.

BRIEF SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

According to a first exemplary embodiment, there is provided a method of forming a probe for a biosensor. The method includes the step of providing a base substrate and forming a platinum layer overlying the base substrate by sputtering platinum, in the absence of oxygen, using a sputtering pressure of at least 30 mtorr.

According to a second exemplary embodiment, there is provided another method of forming a probe for a biosensor. The method includes the step of providing a base substrate and sputtering a first adhesion-promoting layer over the base substrate. The method also includes sputtering a second surface-roughness-promoting layer over the first adhesion-promoting layer and sputtering a platinum third layer over the second surface-roughness-promoting layer, with the platinum third layer being formed by sputtering platinum in the absence of oxygen.

According to a third exemplary embodiment, there is provided a probe for a biosensor. The probe includes a base substrate and a sputtered first adhesion-promoting layer overlying the base substrate. The probe also includes a sputtered second surface-roughness-promoting layer overlying the first adhesion-promoting layer and a sputtered third layer overlying the second surface-roughness-promoting layer. The third layer is a platinum layer.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

FIGS. 5(a) to 5(f) are low magnification scanning electron microscope (SEM) images of the surfaces of probe samples produced using sputtering techniques and electroplating;

FIGS. 6(a) to 6(f) are high magnification SEM images of the surfaces of probe samples produced using sputtering techniques and electroplating;

DETAILED DESCRIPTION

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Figure 1:
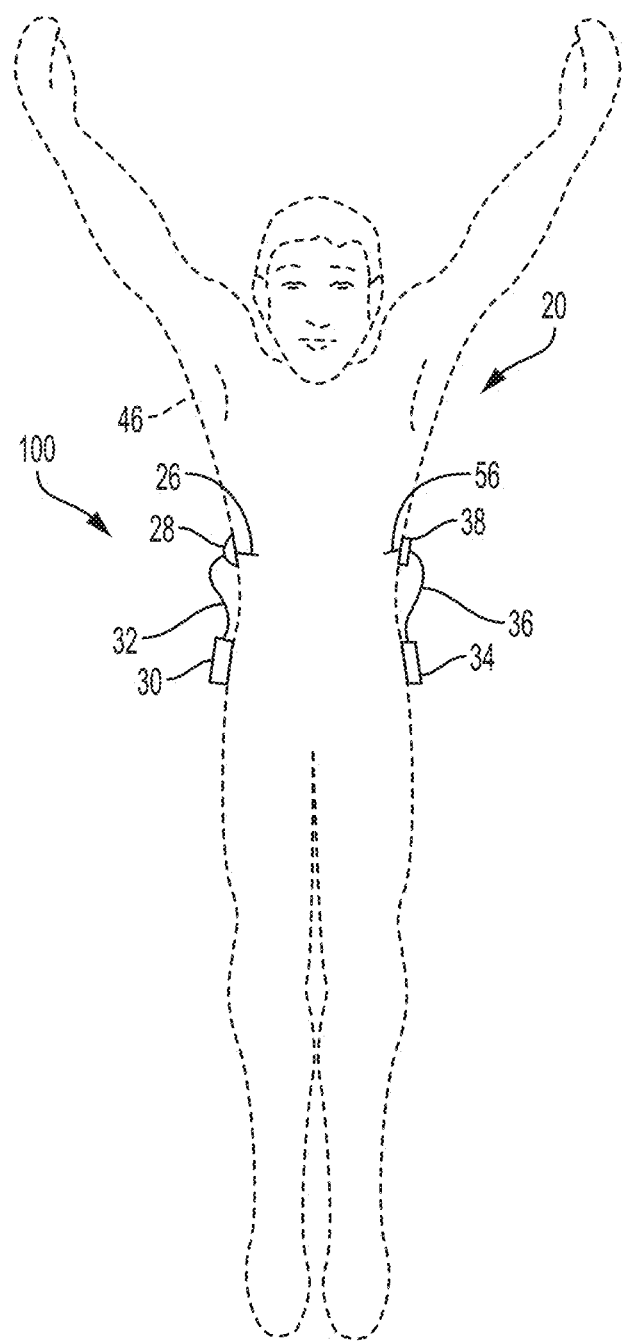
FIG. 1 is a schematic of a location of a glucose biosensor on a user in accordance with an exemplary embodiment.
Figure 2:
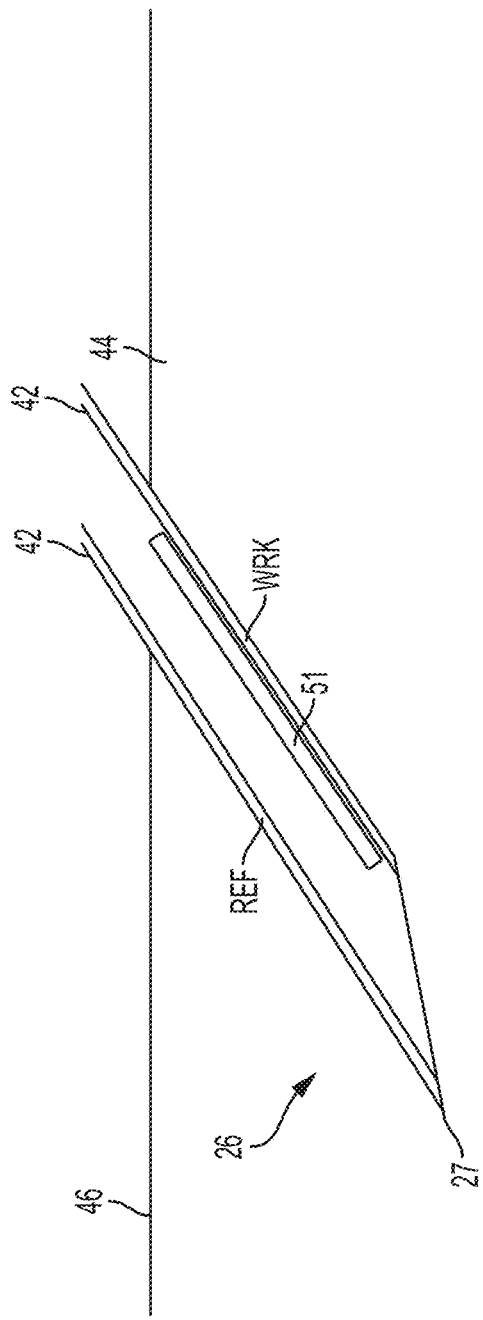
FIG. 2 is a schematic of a probe of a glucose biosensor in accordance with an exemplary embodiment being embedded in a user's skin.

FIG. 1 shows a schematic of a continuous glucose monitoring system 100 being worn by a user 20. In an exemplary embodiment, the glucose monitoring system 100 includes a biosensor 28 having a probe 26, a characteristic monitor 30 and a sensor cable 32. In alternative embodiments, wireless data communication technology can be employed instead of the sensor cable 32. In an exemplary embodiment, the glucose monitoring system may be utilized together with an insulin administration device including an insulin infusion device 34 with an infusion channel 56, an infusion tube 36, and an infusion set 38. Moreover, the characteristic monitor 30 need not be utilized if the insulin infusion device 34 is configured to receive sensor data from the biosensor 28. The probe 26 of the biosensor 28 of the glucose monitoring system 100 is inserted through the skin 46 into a subcutaneous tissue 44 of a user's body 20, as shown in FIG. 2. In an exemplary embodiment, the probe 26 includes a sharpened tip 27 and electrodes 42 which are in contact with interstitial fluid that is present throughout the user's subcutaneous tissue 44. The electrodes 42 include a working electrode WRK and a reference electrode REF. The potential difference between the working electrode WRK and the reference electrode REF caused by the electrochemical oxidation of $H_2O_2$ or the electrochemical reduction of oxygen on the working electrode can be used to determine a $H_2O_2$ or oxygen concentration value, which concentration value can then be used to determine a blood glucose concentration of the user 20. In an exemplary embodiment, the $H_2O_2$ is produced due to the catalyzed reaction of blood glucose to gluconic acid and $H_2O_2$, which is prompted by a catalyst 51 disposed in the proximity of the working electrode WRK. Based on the determined blood glucose concentration, insulin may be administered via the insulin infusion device 34.

Figure 3:
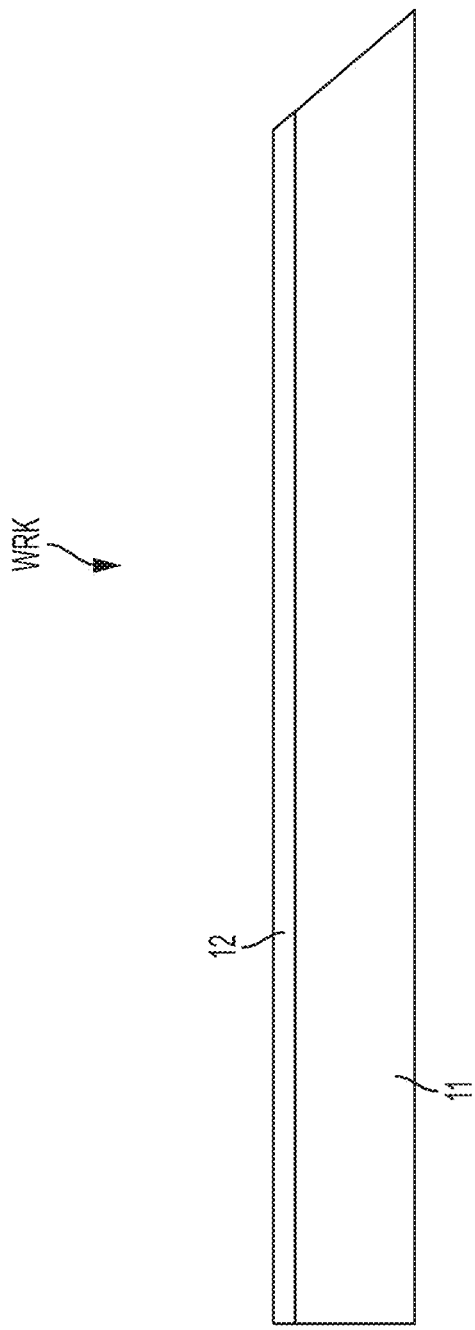
FIG. 3 is a schematic of an electrode of a probe in accordance with an exemplary embodiment.

As shown in FIG. 3, the working electrode WRK has a base substrate 11 and includes a platinum layer 12 disposed on top of the base substrate 11. In an exemplary embodiment, the reference electrode REF has the same configuration. In an exemplary embodiment, the base substrate is polyethylene terephthalate (PET), which is substantially chemically inert, high stiffness material.

It has been recognized by the present inventors that the deposition of a platinum electrode layer 12 on top of the base substrate 11 by conventional techniques such as electroplating is a slow, costly, discontinuous process with several drawbacks. In particular, aside from the time and cost, there is batch-to-batch variability of the working electrode's sensitivity to $H_2O_2$.

It has been recognized by the present inventors that sputtering of a platinum electrode layer onto the base substrate 11 is an alternative to forming the platinum electrode layer by electroplating. However, the present inventors found that conventional sputtering, performed at conventional sputtering powers and pressures, does not result in a probe with a $H_2O_2$ sensitivity that is comparable to a probe with an electroplated electrode layer. This is because conventional sputtering processes result in a "smooth" platinum electrode layer on the base substrate. A "smooth" platinum electrode layer has a reduced surface area as compared to an electroplated platinum electrode layer, and therefore has a reduced area over which electron transfer may be accomplished.

Embodiments described herein relate to probes, and processes for forming probes, where platinum electrode layers are formed sputtering at higher powers and pressures than conventional sputtering.

In particular, it has been discovered by the present inventors that forming platinum electrode layers by sputtering at higher sputtering powers and sputtering pressures improves the $H_2O_2$ sensitivity of the probe to a degree where the sensitivity is comparable with a probe having an electroplated platinum electrode layer. Furthermore, sputtering is a continuous, cheaper process as compared to electroplating, and sputtering is also scalable to larger production loads.

Figure 4:
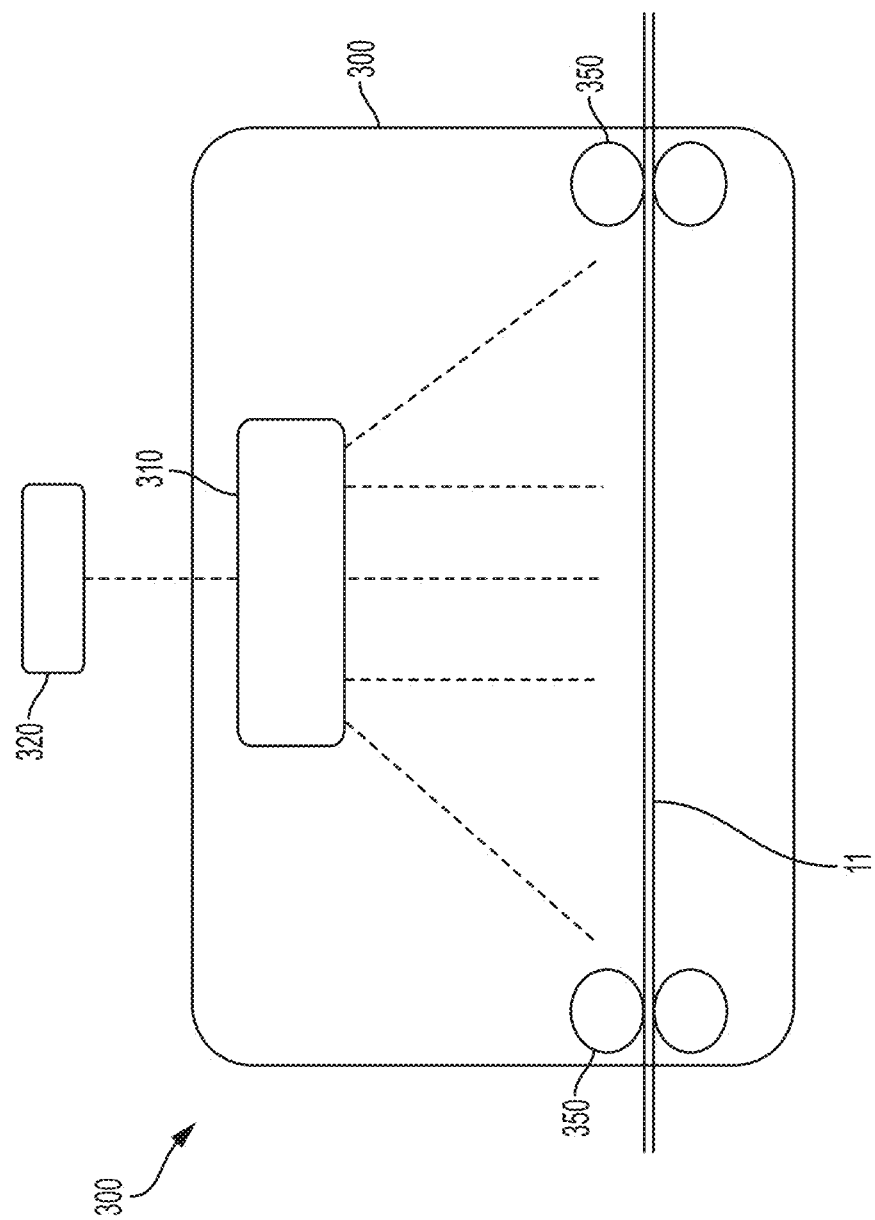
FIG. 4 is a schematic of a continuous sputtering manufacturing process.

FIG. 4 shows an exemplary sputtering machine 300. The sputtering machine 300 includes a sputtering source 310 which is operably connected to a power source 320 configured to supply electrical power to the sputtering source 310. In an exemplary embodiment, the sputtering source 310 includes platinum. The sputtering machine 300 includes a chamber 330 which is filled with an inert gas, for example argon. During sputtering, the inert gas is generally converted into a plasma. In an exemplary embodiment, the sputtering machine 300 also includes a conveyor 350 configured to continuously move a substrate 11 through the chamber 330, so that the substrate 11 can be continuously coated, through sputtering (shown in this figure with dashed lines), by the sputtering source as part of a continuous manufacturing process.

The sputtering pressure inside the chamber 330 and the power of the power source 320 connected to the sputtering source 310 have an effect on the surface morphology of the sputtered layer formed on the surface of the substrate 11. In an exemplary embodiment, the method of sputtering used is specifically gas flow sputtering.

In an exemplary embodiment, the surface of the substrate 11 is plasma pre-treated, for example by corona treatment, before a layer is deposited by sputtering onto the surface of the substrate 11.

In an exemplary embodiment, after the layer has been formed by sputtering on the surface of the substrate 11, laser working is used to shape the sputtered layer into a preferred electrode shape prior to the substrate being used in a probe.

FIGS. 5(a) to 5(e) show low magnification scanning electrode microscope (SEM) images of the surfaces of platinum layers formed on a polyethylene terephthalate (PET) substrate at different sputtering pressures and powers.

FIG. 5(a) shows a platinum layer formed by sputtering at a power of 250 Watts and at a sputtering pressure of about 69 mtorr. The surface roughness ratio of this layer was assessed via an electrochemical CV scan to be about 23.9.

FIG. 5(b) shows a platinum layer formed by sputtering at a power of 250 Watts and at a sputtering pressure of about 50 mtorr. The surface roughness ratio of this layer was assessed via an electrochemical CV scan to be about 23.6.

FIG. 5(c) shows a platinum layer formed by sputtering at a power of 100 Watts and at a sputtering pressure of about 69 mtorr. The surface roughness ratio of this layer was assessed via an electrochemical CV scan to be about 20.2.

FIG. 5(d) shows a platinum layer formed by sputtering at a power of 100 Watts and at a sputtering pressure of about 30 mtorr. The surface roughness ratio of this layer was assessed via an electrochemical CV scan to be about 10.2.

FIG. 5(e) shows a platinum layer formed by sputtering at a lower power and at a sputtering pressure of about 2 mtorr.

The surface roughness ratio of this layer was assessed via an electrochemical CV scan to be about 2.0.

FIG. 5(f) shows a low magnification SEM image of an electroplated "platinum black" electrode layer. The surface roughness ratio of this layer was assessed via an electrochemical CV scan to be about 80.9.

FIGS. 6(a) to 6(e) show high magnification scanning electrode microscope (SEM) images of the surfaces of the same platinum layers shown in FIGS. 3(a) to 3(e). As can be seen in the high magnification SEM images, the surface morphology of the platinum layer is different at higher sputtering powers and pressures than at lower sputtering powers and pressures. In particular, the surface "grains" are larger at higher sputtering powers and pressures than at lower sputtering powers and pressures, contributing to a higher surface roughness ratio.

FIG. 6(f) shows a high magnification SEM image of the electroplated platinum layer.

Figure 7:
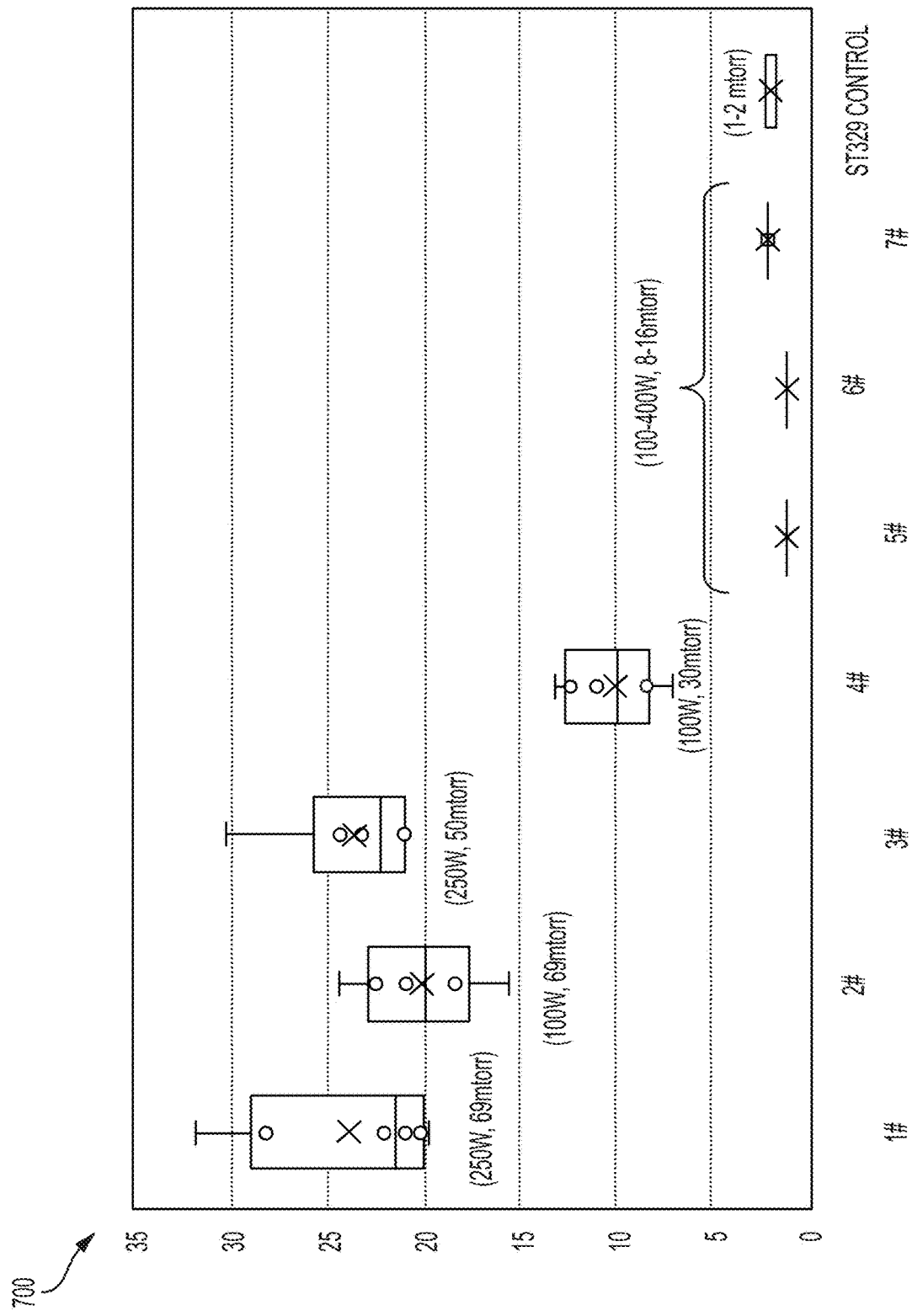
FIG. 7 is a box and whisker chart showing the surface roughness ratios of probes formed by sputtering.

A box and whisker chart 700 of the surface roughness ratio (SAR) values achieved using different sputtering pressures and powers is shown in FIG. 7. As can be seen in FIG. 7, the use of a sputtering pressure of about 30 mtorr or above produces a mean SAR value of around 10 or above, and a sputtering pressure of about 50 mtorr or above produces a mean SAR value of around 20 or above. As used herein, a "medium" sputtering pressure means a sputtering pressure of from about 30 mtorr to about 50 mtorr. As used herein, a "high" sputtering pressure is defined as a sputtering pressure of above about 50 mtorr, and a "low" sputtering pressure is defined as a sputtering pressure of below around 20 mtorr.

As will be explained below, it has been recognized that the use of a high sputtering pressure produces a SAR value which leads to a $H_2O_2$ sensitivity which is comparable to that of electroplated platinum black. Furthermore, it has been recognized that a commercially acceptable $H_2O_2$ sensitivity is achieved with the use of a medium sputtering pressure.

Figure 8:
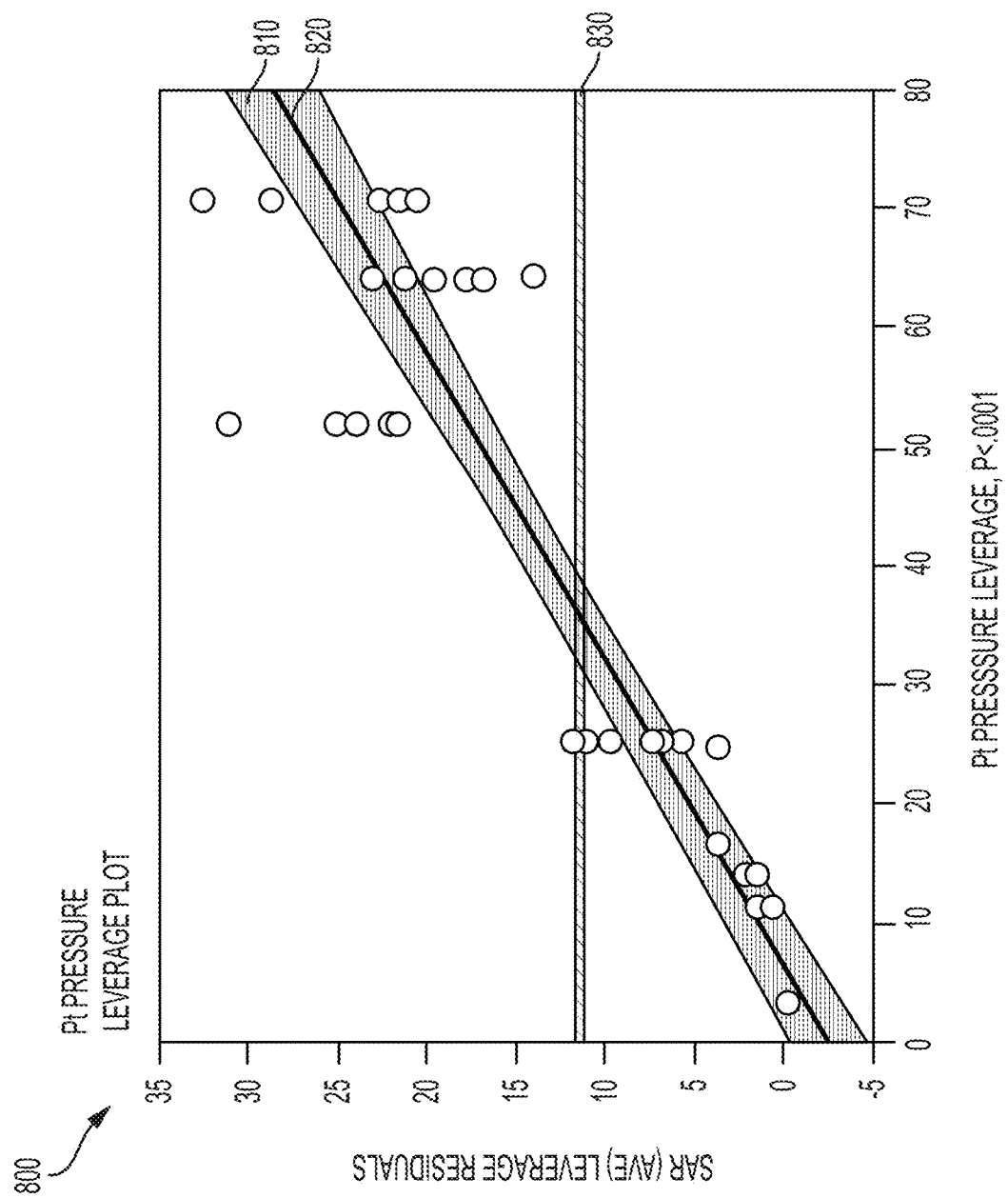
FIG. 8 is a leverage plot showing the effect of sputtering pressure on surface roughness ratio.

FIG. 8 shows a leverage plot 800 showing the effect of sputtering pressure on the SAR value of the deposited layer. As can be seen in FIG. 8, the confidence band 810 of the unconstrained model 820 does not encompass the constrained model 830, thereby indicating that the sputtering pressure has an effect on the SAR value of the samples.

Figure 9:
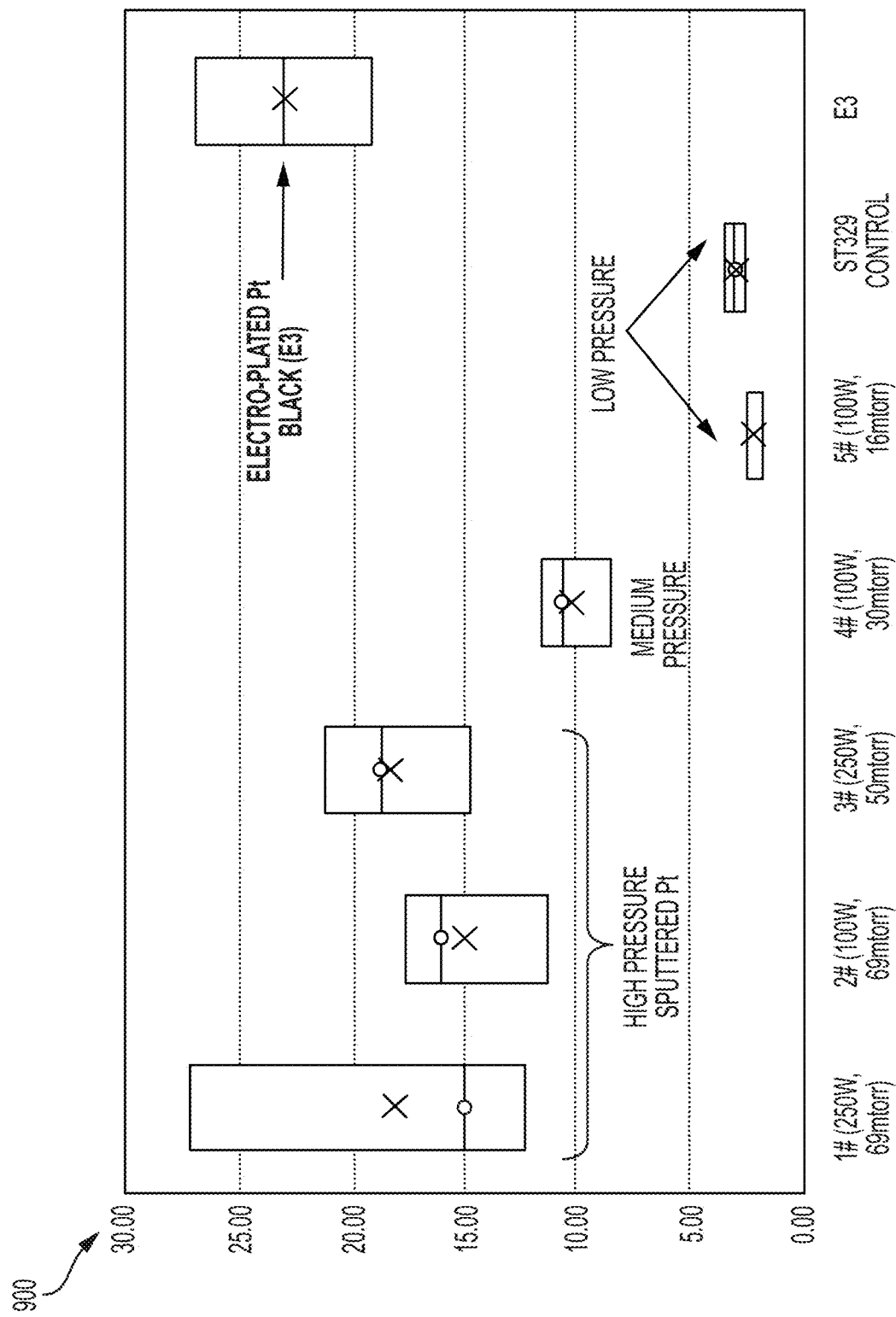
FIG. 9 is a graph showing the $H_2O_2$ sensitivities of various probes formed using sputtering.

FIG. 9 is a graph 900 showing the $H_2O_2$ sensitivity of sputtered platinum layers formed under various conditions as compared to the $H_2O_2$ sensitivity of an electroplated platinum "black" layer. As can be seen in FIG. 7, the $H_2O_2$ sensitivity of a sputtered platinum layer formed at a sputtering power of 250 W and 69 mtorr is comparable to, and in some cases higher than, the $H_2O_2$ sensitivity of the electroplated platinum "black" layer, even though the SAR value of the high pressure sputtered platinum layer is lower than the SAR of the electroplated platinum black.

Without wishing to be bound by theory, it is believed that the comparable levels of $H_2O_2$ sensitivity is due to the formation of "black" platinum oxide during the electroplating process, which acts to decrease the $H_2O_2$ sensitivity of the platinum layer. Since, at most, only negligible amounts of platinum oxide are formed in the predominantly inert gas atmosphere used during the sputtering process, $H_2O_2$ sensitivity is not limited due to oxide formation in the sputtered layers, thereby leading to a comparable $H_2O_2$ sensitivity with a lower SAR value. As such, if a sufficiently high sputtering pressure and power were to be used to achieve a sputtered platinum layer having a SAR value similar to that of electroplated platinum "black", the sputtered platinum layer would have a higher sensitivity to $H_2O_2$ as compared to the electroplated platinum "black".

FIG. 9 also shows that a "medium" sputtering pressure of 30 mtorr results in an average $H_2O_2$ sensitivity of around 10 nA/µM mm$^2$, which is an acceptable sensitivity for biosensor applications. As such, the cost and time benefits associated with sputtering deposition of layers as compared to the electroplating of layers are realized even at "medium" sputtering pressures.

The thickness of the sputtered platinum layer is preferably between 15 and 2000 nm, for example between 20 and 1000 nm, such as between 25 and 100 nm.

In exemplary embodiments, the thickness of the sputtered platinum layer is measured during the continuous sputtering process. If a current is applied along a pre-determined distance of the platinum-layered substrate at a pre-determined voltage, the majority of the current will flow along the platinum layer, since platinum has a much lower resistivity than the PET substrate. The thickness of the platinum layer can then be determined from the obtained resistance value, the length across which the current is applied and the cross-sectional area of the base substrate. In this manner, dynamic measurements may be performed to monitor, in real-time, the thickness of the platinum layer.

Figure 10:
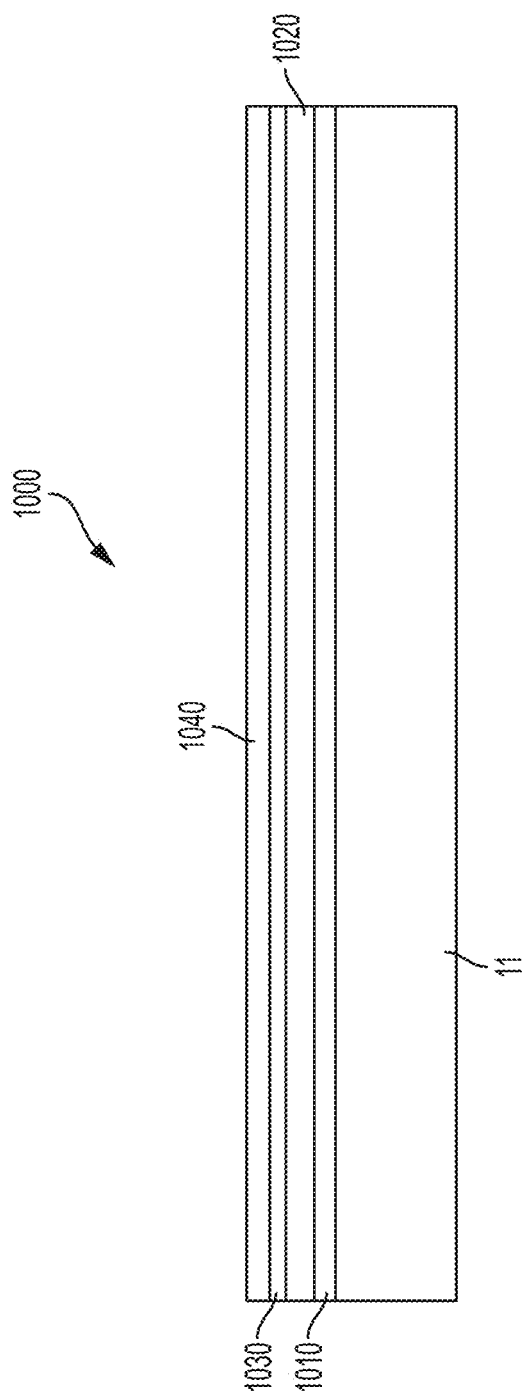
FIG. 10 is a probe including a sputtered tri-layer structure in accordance with an exemplary embodiment.

Exemplary embodiments disclosed herein also relate to the sputtering of multiple layers onto a base substrate in order to form a probe. FIG. 10 shows a schematic of such a multi-layered probe 1000.

Multi-layered probe 1000 includes a sputtered first layer 1010 overlying a base substrate 11. In exemplary embodiments, the sputtered first layer 1010 is an adhesion-promoting layer that is configured to promote adhesion of further sputtered layers overlying the first layer 1010 to the base substrate 11. In exemplary embodiments, the sputtered first layer is titanium. In other exemplary embodiments, the sputtered first layer is chromium. In exemplary embodiments the sputtered first layer is between about 5 nm to about 100 nm, for example between about 10 and about 30 nm.

It has been discovered that the provision of a titanium or chromium first adhesion-promoting layer decreases the likelihood that further sputtered layers delaminate from the base substrate.

In an exemplary embodiment, the multi-layered probe 1000 further comprises a sputtered second layer 1020 adjacent to the sputtered first layer 1010. In exemplary embodiments, the sputtered second layer is formed by reactively sputtering with a platinum sputtering source in a controlled flow of argon and oxygen gas so as to form a platinum oxide sputtered layer. In exemplary embodiments, the sputtered second layer has a thickness of between about 20 nm and 2000 nm, for example between about 50 nm to about 80 nm. The surface roughness of the platinum oxide second sputtered layer can be controlled through control of the oxygen/argon flow; the sputtering pressure and the sputtering power.

In particular, it is possible to achieve a high surface roughness ratio (SAR) value with the sputtered platinum oxide second layer 1020, since the formation of oxides on the surface layer acts to increase the surface roughness by disrupting the surface morphology of the sputtered layer. The second sputtered layer 1020 may therefore be used to promote the surface-roughness of further sputtered layers overlying the second sputtered surface-roughness-promoting layer 1020.

In another exemplary embodiment, the sputtered second layer is formed by reactively sputtering with an iridium (Ir) or ruthenium (Ru) sputtering source in a controlled flow of argon and oxygen gas so as to form an iridium oxide ($IrO_x$) or ruthenium oxide ($RuO_x$) sputter layer. In exemplary embodiments, the sputtered second layer has a thickness of between about 20 nm and 2000 nm, for example between about 50 nm to about 80 nm. The surface roughness of the iridium oxide or ruthenium oxide second sputtered layer can also be controlled through control of the oxygen/argon flow; the sputtering pressure and the sputtering power.

In particular, it is possible to achieve a high surface roughness ratio (SAR) value with the sputtered iridium oxide or ruthenium oxide second layer 1020, since the formation of oxides on the surface layer acts to increase the surface roughness by disrupting the surface morphology of the sputtered layer. The second sputtered layer 1020 may therefore be used to promote the surface-roughness of further sputtered layers overlying the second sputtered surface-roughness-promoting layer 1020.

In an exemplary embodiment, the multi-layered probe further comprises a sputtered third layer 1030 adjacent to the sputtered second surface-roughness-promoting layer 1020. In exemplary embodiments, the sputtered third layer is a platinum layer that serves as an active layer for electrochemical sensing of the oxidation of $H_2O_2$ or the reduction of O2. In an exemplary embodiment, the thickness of the platinum layer is between around 25 nm and around 100 nm.

By sputtering a platinum third layer 1030 on top of the sputtered surface-roughness promoting second layer 1020, the surface roughness of the sputtered platinum third layer 1030 may be increased as a result of the relatively high surface roughness of the underlying second sputtered layer 1020. In other words, the second sputtered layer 1020 is used to promote an increased surface roughness ratio of the overlying third sputtered layer 1030. Without wishing to be bound by theory, it is believed that third sputtered platinum layer 1030 follows the contours of the oxide formed on the second surface-roughness-promoting layer 1020, thereby increasing the surface roughness of the third sputtered platinum oxide layer 1030.

In an exemplary embodiment, the sputtering pressure used during sputter formation of the third layer is in excess of 30 mtorr. As explained above, the use of a sputtering pressure above 30 mtorr increases the SAR value of the platinum third layer 1030. The increased SAR value of the platinum third layer 1030 resulting from the surface-roughness-promoting second layer 1020 is therefore further increased through the use of a sputtering pressure of above 30 mtorr.

In yet another exemplary embodiment, the second surface-roughness-promoting layer 1020 is not formed of platinum oxide, iridium oxide or ruthenium oxide. Instead, the second surface-roughness-promoting layer 1020 may be formed through sputtering zirconium in an argon/oxygen gas mixture (to thereby form a zirconium oxide second sputtered layer) or by sputtering ruthenium in an argon/oxygen mixture (to thereby form a ruthenium oxide second sputtered layer).

It has been observed by the inventors that platinum oxide, ruthenium oxide, iridium oxide and zirconium oxide all act to promote surface roughness of a subsequently sputtered platinum layer 1030 overlying the second sputtered layer 1020. Furthermore, it has been observed that platinum, iridium, ruthenium and zirconium can form oxides during the sputtering process without difficulty, when sputtered in the presence of oxygen.

The multi-layered probe 1000 having first 1010, second 1020, and third 1030 sputtered layers has been observed to have improved stability characteristics, with the three layers adhering strongly to the base substrate.

In an exemplary embodiment, a catalyst 1040, for example an enzymatic catalyst, is disposed overlying the third sputtered layer 1030, the catalyst 1040 being for promotion of the reaction steps from blood glucose to $H_2O_2$.

In exemplary embodiments, each one of the first 1010, second 1020 and third 1030 layers are formed with a "one-pass" sputtering technique, where multiple sputtering procedures to form a single layer are avoided. In an embodiment, the type of sputtering used to form each one of the first 1010, second 1020 and third 1030 layers is gas-flow sputtering. In an embodiment, three separate sputtering chambers are used to form the three sputtered layers.

Figure 11:
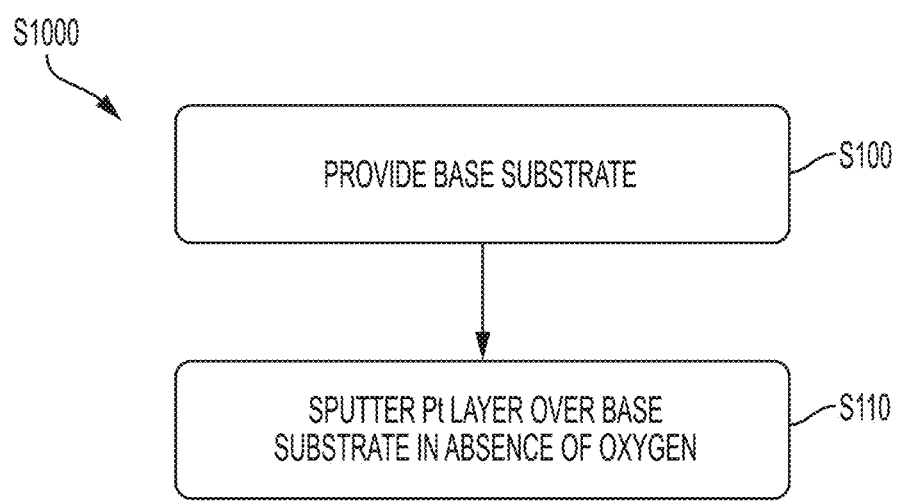
FIG. 11 is a flowchart of a method according to an exemplary embodiment.

FIG. 11 shows a flowchart of a method S1000 of forming a probe for a biosensor in accordance with an exemplary embodiment. At step S100, a base substrate is provided. After provision of the base substrate, the method progresses to step S110. At step S110, a platinum layer is formed overlying the base substrate by sputtering in the absence of oxygen. The platinum sputtering to form the base layer is performed at a sputtering pressure of at least 30 mtorr, for example at least 50 mtorr. In an exemplary embodiment, the platinum layer is formed to have a thickness of between 15 nm and 2000 nm. In an exemplary embodiment, the sputtering power used during the sputtering is at least 100 W. In an exemplary embodiment, polyethylene terephthalate (PET) is used as the base substrate. In an exemplary embodiment, the method of FIG. 11 is a continuous process.

Figure 12:
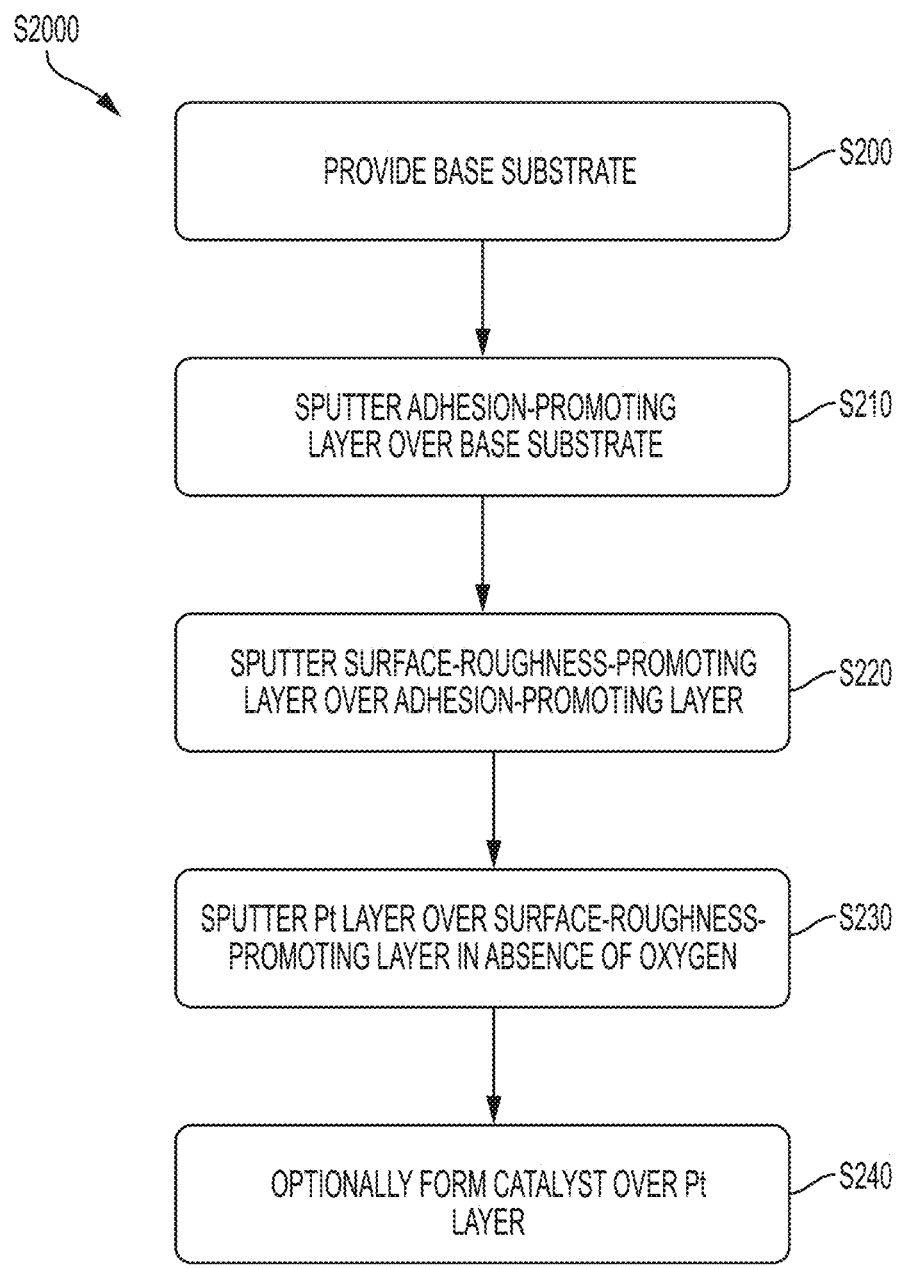
FIG. 12 is another flowchart of a method according to an exemplary embodiment.

FIG. 12 shows a flowchart of a method S2000 of forming a probe for a biosensor in accordance with an exemplary embodiment. At step S200, a base substrate is provided. In an exemplary embodiment, the step S200 of providing the base substrate comprises providing a base substrate formed from polyethylene terephthalate (PET). After provision of the base substrate, the method progresses to step S210.

At step S210, a first adhesion-promoting layer is sputtered over the base substrate. In an exemplary embodiment, the step of sputtering the first layer S210 onto the base substrate comprises sputtering a titanium first layer onto the base substrate. The method then progresses to step S220.

At step S220, a second surface-roughness promoting layer is sputtered onto the first layer. In an exemplary embodiment, the step of sputtering the second layer S220 onto the first layer comprises sputtering a platinum layer onto the first layer in the presence of oxygen. In exemplary embodiment, the step of sputtering the second layer S220 is performed by gas flow sputtering. The method then progresses to step S230.

At step S230, a platinum third layer is sputtered over the second surface-roughness-promoting layer in the absence of oxygen. In an exemplary embodiment, the step of sputtering the third layer S230 comprises sputtering a platinum third layer having a thickness of between 25 nm and 100 nm. In an exemplary embodiment, the step S230 of sputtering the platinum third layer onto the second layer is performed at a sputtering pressure of above 30 mtorr. The method then optionally progress to step S240.

At step S240, a catalyst is formed on the platinum layer. In an exemplary embodiment, the catalyst is an enzyme.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

In addition, certain terminology may also be used in the following description for the purpose of reference only, and thus are not intended to be limiting. For example, terms such as "upper", "lower", "above", and "below" refer to directions in the drawings to which reference is made. Terms such as "front", "back", "rear", "side", "outboard", and "inboard" describe the orientation and/or location of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second", and other such numerical terms referring to structures do not imply a sequence or order unless clearly indicated by the context.

For the sake of brevity, conventional techniques related to biosensor probe manufacturing may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of forming a probe for a glucose biosensor, the method comprising the steps of:
    providing a base substrate;
    sputtering a first adhesion-promoting layer overlying the base substrate;
    sputtering a second surface-roughness-promoting layer overlying the first adhesion-promoting layer, wherein the sputtering of the second surface-roughness-promoting layer is in presence of oxygen using a sputtering source comprising a material selected from the group of platinum, iridium, ruthenium, and zirconium, and wherein the second surface-roughness-promoting layer has a thickness from 20 nm to 200 nm; and
    sputtering a platinum third layer overlying the second surface-roughness-promoting layer, the platinum third layer being formed by sputtering platinum in absence of oxygen;
wherein the method is a continuous process using a conveyor to continuously move the base substrate through a sputtering chamber during sputtering in the sputtering chamber.

2. The method of claim 1, wherein the step of sputtering the first adhesion-promoting layer overlying the base substrate comprises sputtering a titanium layer overlying the base substrate.

3. The method of claim 1, wherein the step of sputtering the second surface-roughness-promoting layer is performed by gas flow sputtering.

4. The method of claim 1, wherein the step of providing the base substrate comprises providing a base substrate formed from polyethylene terephthalate (PET).

5. The method of claim 1, wherein the step of sputtering the platinum third layer overlying the second surface-roughness-promoting layer comprises sputtering a platinum third layer having a thickness of between 25 nm and 100 nm.

6. The method of claim 1, wherein the step of sputtering the platinum third layer overlying the second layer is performed at a sputtering pressure of above 30 mtorr.

7. The method of claim 1, wherein the sputtering the platinum third layer comprises sputtering the platinum third layer having a thickness of between 15 nm and 2000 nm.

8. The method of claim 1, wherein the sputtering the platinum third layer comprises sputtering the platinum third layer using a sputtering power of at least 100 W.

9. The method of claim 1, wherein the platinum third layer is sputtered using a sputtering pressure of at least 50 mtorr.

10. The method of claim 1, wherein the first adhesion-promoting layer has a thickness of from 5 nm to 100 nm.

* * * * *